US012661327B2

(12) United States Patent (10) Patent No.: US 12,661,327 B2

Inazuki (45) Date of Patent: Jun. 23, 2026

(54) AQUEOUS PATCH

(71) Applicant: TEIKOKU SEIYAKU CO., LTD., Kagawa (JP)

(72) Inventor: Masahiro Inazuki, Kagawa (JP)

(73) Assignee: TEIKOKU SEIYAKU CO., LTD., Kagwa (JP)

( * ) Notice: Subject to any disclaimer, the term of this patent is extended or adjusted under 35 U.S.C. 154(b) by 355 days.

(21) Appl. No.: 17/621,582

(22) PCT Filed: Jun. 15, 2020

(86) PCT No.: PCT/JP2020/023346

§ 371 (c)(1),
(2) Date: Dec. 21, 2021

(87) PCT Pub. No.: WO2020/262057

PCT Pub. Date: Dec. 30, 2020

(65) Prior Publication Data

US 2022/0354804 A1 Nov. 10, 2022

(30) Foreign Application Priority Data

Jun. 24, 2019 (JP) ................................ 2019-116551

(51) Int. Cl.

| *A61K 9/70* | (2006.01) |
| *A61K 9/00* | (2006.01) |
| *A61K 31/045* | (2006.01) |
| *A61K 31/167* | (2006.01) |
| *A61K 31/192* | (2006.01) |
| *A61K 45/06* | (2006.01) |
| *A61K 47/02* | (2006.01) |
| *A61K 47/10* | (2017.01) |
| *A61K 47/44* | (2017.01) |
| *A61P 23/02* | (2006.01) |
| *A61P 25/02* | (2006.01) |
| *A61P 29/00* | (2006.01) |

(52) U.S. Cl.

CPC .......... *A61K 9/7023* (2013.01); *A61K 9/0014* (2013.01); *A61K 9/7046* (2013.01); *A61K 9/7053* (2013.01); *A61K 9/7061* (2013.01); *A61K 31/045* (2013.01); *A61K 31/167* (2013.01); *A61K 31/192* (2013.01); *A61K 45/06* (2013.01); *A61K 47/02* (2013.01); *A61K 47/10* (2013.01); *A61K 47/44* (2013.01); *A61P 23/02* (2018.01); *A61P 25/02* (2018.01); *A61P 29/00* (2018.01)

(58) Field of Classification Search

None
See application file for complete search history.

(56) References Cited

U.S. PATENT DOCUMENTS

| 4,931,283 A | 6/1990 | Tsuk |
| 4,933,184 A | 6/1990 | Tsuk |
| 2002/0045923 A1 | 4/2002 | Tone et al. |
| 2004/0098072 A1 | 5/2004 | Tone et al. |
| 2005/0034925 A1 | 2/2005 | Flamang et al. |
| 2006/0194759 A1* | 8/2006 | Eidelson .............. A61K 31/728 514/171 |
| 2007/0036847 A1 | 2/2007 | Yoshinaga et al. |
| 2008/0207560 A1* | 8/2008 | Harada .................. A61K 8/553 514/474 |
| 2009/0004256 A1 | 1/2009 | Yoshinaga et al. |
| 2009/0123527 A1* | 5/2009 | Alam ................... A61K 9/7084 514/626 |
| 2015/0246153 A1* | 9/2015 | Ota ........................ A61L 15/26 524/81 |
| 2018/0291160 A1* | 10/2018 | Shimakawa ............ C08L 83/04 |

FOREIGN PATENT DOCUMENTS

| CN | 110478334 A | * 11/2019 | .......... A61K 31/167 |
| EP | 1 181 911 | 3/2006 | |
| EP | 1 666 032 | 6/2006 | |
| JP | 60-152413 | 8/1985 | |
| JP | 63-222113 | 9/1988 | |
| JP | 5-310598 | 11/1993 | |
| JP | 11-199475 | 7/1999 | |
| JP | 2001-302501 | 10/2001 | |
| JP | 2001-302501 A | * 10/2001 | |
| JP | 2002-154950 | 5/2002 | |
| JP | 2005-179312 | 7/2005 | |
| JP | 2007-39451 | 2/2007 | |
| WO | 2013/191293 | 12/2013 | |
| WO | WO 2013/191293 A1 | * 12/2013 | |
| WO | WO-2019098327 A1 | * 5/2019 | ......... A61K 31/4725 |

OTHER PUBLICATIONS

English translation for JP2007-039451A (Year: 2007).*
Nakahashi et al ("The role of light anhydrous silicic acid on physical stability of troglitazone solid dispersion under humidified conditions", Advanced Powder Technology, vol. 25 (2014), p. 716-721 (Year: 2014).*
English translation for JP WO 2013/191293 A1 (2013).*
English translation for JP 2001-302501 A (2001).*
English translation for JP 2007-39451A (Year: 2007).*
English translation for JP 63-222113 obtained from Espacenet (1988).*

(Continued)

*Primary Examiner* — Sin J Lee

(74) *Attorney, Agent, or Firm* — Wenderoth, Lind & Ponack, L.L.P.

(57) ABSTRACT

The purpose of the present invention is to provide an aqueous patch in which basic physical properties as an aqueous patch are less likely to deteriorate and crystals of 1-menthol are less likely to precipitate. The aqueous patch includes, in a pasty preparation, 1-menthol: 0.5% by mass or more and 10% by mass or less, an oil component: 0.2% by mass or more and 19% by mass or less; and silica: 0.1% by mass or more and 5.5% by mass or less.

6 Claims, No Drawings

(56)         References Cited

OTHER PUBLICATIONS

English translation for JP 63-222113 obtained from Google (1988).*
English translation for WO 2019/098327A1 obtained from Google (2019).*
Fulton ("Comedogenicity and irritancy of commonly used ingredients in skin care products", J. Soc. Cosmet. Chem., vol. 40, p. 321-333 (Nov./Dec. 1989)) (Year: 1989).*
Vieira et al.("Effect of ricinoleic acid in acute and subchronic experimental models of inflammation", Mediators of Inflammation, vol. 9 , p. 223-228 (2000)) (Year: 2000).*
English translation for CN-110478334-A (2019).*
Extended European Search Report issued Mar. 16, 2023 in corresponding European Patent Application No. 20833694.1.

First Notification of Office Action issued Aug. 10, 2023 in corresponding Chinese Patent Application No. 202080045193.6, with English language translation.
International Search Report issued Jul. 14, 2020 in International (PCT) Application No. PCT/JP2020/023346.
Office Action issued May 21, 2024 in Chinese Patent Application No. 202080045193.6, with English-language Translation.
Office Action dated Jan. 23, 2024 in corresponding Japanese Patent Application No. 2021-528204 with English language translation.
Office Action dated Jan. 25, 2024 in corresponding Chinese Patent Application No. 202080045193.6 with English language translation.
Office Action issued Sep. 15, 2025 in European Patent Application No. 20 833 694.1.

* cited by examiner

AQUEOUS PATCH

TECHNICAL FIELD

The present invention relates to an aqueous patch containing 1-menthol.

BACKGROUND ART

Conventionally, menthol has been blended as a refreshing agent in an external preparation containing a local anesthetic or an anti-inflammatory drug, and the like. For example, in the case of a commercially available preparation, menthol was blended in the preparation in a ratio of about 1% by mass or less.

Various menthol-containing external preparations as described above have been known. For example, Patent Document 1 discloses a water-containing patch for treatment of knee joint pain, stiff shoulder, and the like containing lidocaine in which 1-menthol is blended in a ratio of 0.75% by mass. Also, Patent Document 2 discloses a felbinac-containing poultice in which 1-menthol is blended in a ratio of 0.5% by mass. Furthermore, Patent Document 3 discloses a transdermal dosage form preparation in which menthol is blended in a ratio of about 4% by weight to 16% by weight. Patent Document 4 discloses a patch in which 1-menthol is blended in a ratio of 0.1 to 4% by weight of 1-menthol or mentha oil.

RELATED ART DOCUMENT

Patent Documents

Patent Document 1: JP-A-2001-302501
Patent Document 2: JP-A-2005-179312
Patent Document 3: JP-A-S60-152413
Patent Document 4: JP-A-H5-310598

SUMMARY OF THE INVENTION

Problems to be Solved by the Invention

As described above, various aqueous patches containing 1-menthol have been known so far, but since 1-menthol has low solubility in an aqueous base, there is a possibility that crystals of 1-menthol are precipitated in a conventional aqueous patch. The present invention has been made in view of the above circumstances, and an object of the present invention is to provide an aqueous patch in which basic physical properties as an aqueous patch are less likely to deteriorate and crystals of 1-menthol are less likely to precipitate.

Solutions to the Problems

The aqueous patch according to an embodiment of the present invention that has been able to solve the above problems has any one of the following configurations.

[1] An aqueous patch including, in a pasty preparation.
1-menthol: 0.5% by mass or more and 10% by mass or less,
an oil component: 0.2% by mass or more and 19% by mass or less; and
silica: 0.1% by mass or more and 5.5% by mass or less.
[2] The aqueous patch according to above [1], further including, in the pasty preparation,
drug: 0.5% by mass or more and 10% by mass or less, wherein the drug is at least one selected from the group consisting of local anesthetic and pharmaceutically acceptable salt thereof.
[3] The aqueous patch according to above [2], wherein a total ratio of mass of the drug and mass of the 1-menthol to mass of the oil component is 0.10 or more and 12 or less.
[4] The aqueous patch according to above [1], including, in the pasty preparation,
drug: 0.3% by mass or more and 5% by mass or less,
wherein the drug is at least one selected from the group consisting of anti-inflammatory drug and pharmaceutically acceptable salt thereof.
[5] The aqueous patch according to above [4], wherein a total ratio of mass of the drug and mass of the 1-menthol to mass of the oil component is 0.10 or more and 6 or less.
[6] The aqueous patch according to any one of above [1] to [5], wherein a ratio of mass of the silica to mass of the oil component is 0.06 or more.
[7] The aqueous patch according to any one of above [1] to [6], further including, in the pasty preparation, a water-soluble polymer material, wherein a ratio of mass of the water-soluble polymer material to mass of the oil component is 0.65 or more.
[8] The aqueous patch according to any one of above [1] to [7], wherein the silica is a powder having a specific surface area of 30 $m^2/g$ or more and 420 $m^2/g$ or less as measured by a specific surface area measurement method specified in JIS Z 8830.
[9] The aqueous patch according to any one of above [1] to [8], wherein the oil component is at least one selected from the group consisting of vegetable oil, animal oil, hydrocarbon, fatty acid, fatty acid ester, silicon oil, high molecular weight polyethylene glycol, crotamiton, deet, and vitamin E derivative.

Effects of the Invention

According to the present invention, with the above configuration, it is possible to provide an aqueous patch in which basic physical properties as an aqueous patch less likely to deteriorate and crystals of 1-menthol are less likely to precipitate.

MODE FOR CARRYING OUT THE INVENTION

The aqueous patch of the embodiment of the present invention contains, in a pasty preparation, 1-menthol: 0.5% by mass or more and 10% by mass or less, an oil component: 0.2% by mass or more and 19% by mass or less; and silica: 0.1% by mass or more and 5.5% by mass or less.

First, the present inventors have found that, by blending a predetermined amount of an oil component into a predetermined amount of 1-menthol in an aqueous pasty preparation, crystals of 1-menthol are less likely to precipitate. On the other hand, it has been found that when an oil component is blended in an aqueous pasty preparation, the pasty preparation may bleed through from a base fabric at the time of production, or emulsion may break after long-term storage and the oil component may exude from the base fabric, leading to deterioration in shape retaining properties and adhesiveness. As a result of intensive studies on such problems, the present inventor has found that when a predetermined amount of silica is blended in an aqueous pasty preparation, exudation of the oil component can be reduced, and further, shape retaining properties and adhesiveness can be maintained. That is, according to the aqueous patch of the embodiment of the present invention, it is possible to maintain a relatively high concentration of 1-menthol in a dissolved state for a long period of time while having the shape retaining properties and adhesiveness of a pasty preparation which are basic physical properties as an aqueous patch.

Hereinafter, each component constituting the aqueous patch of the embodiment of the present invention will be described in detail.

[1-Menthol]

When 1-menthol is contained in the pasty preparation, effects such as analgesic properties, local anesthetic properties, and antipruritic properties are exhibited. When 1-menthol is blended, it may be blended in the form of mentha oil, mint oil, perfume containing 1-menthol, or the like. When 1-menthol is blended in the form of mentha oil, mint oil, or the like, the content of 1-menthol can be calculated based on the content of contained 1-menthol.

The content of 1-menthol in the pasty preparation is 0.5% by mass or more and 10% by mass or less. When the content of 1-menthol is 0.5% by mass or more, effects such as analgesic properties, local anesthetic properties, and antipruritic properties are easily exhibited. Further, a function of improving skin permeability of a drug by 1-menthol is easily exhibited. The content of 1-menthol is preferably 1.0% by mass or more, more preferably 2.0% by mass or more, further preferably 2.5% by mass or more, still more preferably 3.5% by mass or more, and particularly preferably 4.0% by mass or more. On the other hand, when the content of 1-menthol is 10% by mass or less, crystals of 1-menthol are less likely to precipitate. Furthermore, the pasty preparation becomes uniform, and adhesive force is easily improved. The content of 1-menthol is preferably 8.5% by mass or less, more preferably 7.0% by mass or less, further preferably 6.0% by mass or less, still more preferably 5.5% by mass or less, and particularly preferably 5.0% by mass or less.

[Oil Component]

The oil component is preferably at least one selected from the group consisting of vegetable oil, animal oil, hydrocarbon, fatty acid, fatty acid ester, silicon oil, high molecular weight polyethylene glycol, crotamiton, deet, and vitamin E derivative. These can be used singly or in combination of two or more kinds. The high molecular weight polyethylene glycol means a polyethylene glycol having a weight average molecular weight of 1000 or more. Furthermore, the oil component is more preferably at least one selected from the group consisting of vegetable oil, hydrocarbon, fatty acid, fatty acid ester, crotamiton, and vitamin E derivative, further preferably at least one selected from the group consisting of vegetable oil, fatty acid, and fatty acid ester, and particularly preferably at least one selected from the group consisting of vegetable oil and fatty acid ester. By blending the oil components, 1-menthol is easily dissolved, and even when a relatively high concentration of 1-menthol is blended in the pasty preparation, precipitation of crystals of 1-menthol can be easily suppressed over a long period of time.

Examples of the vegetable oil include corn oil, sesame oil, olive oil, almond oil, peanut oil, rapeseed oil, soybean oil, and the like. These can be used singly or in combination of two or more kinds.

Examples of the animal oil include squalene and squalane. These can be used singly or in combination of two or more kinds.

Examples of the hydrocarbon include liquid paraffin, polybutene, polyisoprene, and the like. These can be used singly or in combination of two or more kinds.

Examples of the fatty acid include isostearic acid, oleic acid, palmitic acid, and the like. These can be used singly or in combination of two or more kinds.

Examples of the fatty acid ester include isopropyl myristate, glycerin fatty acid ester such as castor oil, sorbitol fatty acid ester, polyethylene glycol fatty acid ester, and the like. These can be used singly or in combination of two or more kinds.

Examples of the vitamin E derivative include tocopherol acetate and the like.

The content of the oil component in the pasty preparation is 0.2% by mass or more and 19% by mass or less. When the content of the oil component is 0.2% by mass or more, high concentration 1-menthol is easily dissolved at the time of blending, and precipitation of crystals of 1-menthol over time can be easily prevented. Therefore, the content of the oil component is preferably 0.5% by mass or more, more preferably 1.0% by mass or more, further preferably 2.0% by mass or more, still more preferably 3.0% by mass or more, and particularly preferably 4.0% by mass or more. On the other hand, when the content of the oil component is 19% by mass or less, the oil component is less likely to exude from the base fabric, and shape retaining properties of the pasty preparation can be easily improved. Therefore, the content of the oil component is preferably 17% by mass or less, more preferably 15% by mass or less, further preferably 13% by mass or less, still more preferably 10% by mass or less, and particularly preferably 8% by mass or less.

The oil component preferably has a viscosity at 20° C. of 15 mPa·s or more and 2000 mPa·s or less, more preferably 30 mPa·s or more and 1500 mPa·s or less, and further preferably 50 mPa·s or more and 1000 mPa·s or less, as measured by a viscometer measuring method using a capillary viscometer of JIS Z 8803. Whereby, it is possible to easily achieve both the prevention of the precipitation of crystals of 1-menthol and the improvement in shape retaining properties of the pasty preparation.

In the pasty preparation, a ratio of mass of the oil component to mass of the 1-menthol (mass of the oil component/mass of the 1-menthol) is preferably 0.5 or more and 1.9 or less. When the ratio is 0.5 or more, crystals of 1-menthol are less likely to precipitate, and the skin permeability of the drug is easily improved. Therefore, the ratio is more preferably 1.0 or more, and further preferably 1.2 or more. On the other hand, when the ratio is 19 or less, the oil component is less likely to exude from the base fabric. Therefore, the ratio is more preferably 15 or less, further preferably 10 or less, still more preferably 5 or less, and particularly preferably 3 or less.

[Silica]

Examples of the silica include light silica. As the light silica, one described in the Japanese Pharmacopoeia as "light anhydrous silicic acid" can be used.

The silica is preferably a powder having a specific surface area of 30 m²/g or more and 420 m²/g or less as measured by a specific surface area measurement method specified in JIS Z 8830. When the silica has a specific surface area of 30 m²/g or more, exudation of the pasty preparation can be easily prevented. Therefore, the silica has a specific surface area of more preferably 50 m²/g or more, and further preferably 100 m²/g or more. On the other hand, when the silica has a specific surface area of 420 m²/g or less, secondary aggregation can be easily prevented. Therefore, the silica has a specific surface area of more preferably 400 m²/g or less, and further preferably 380 m²/g or less. Silica may have a hydrophobic surface, but preferably has a hydrophilic surface.

The content of the silica in the pasty preparation is 0.1% by mass or more and 5.5% by mass or less. When the content of silica is 0.1% by mass or more, exudation of the pasty preparation can be easily prevented. Therefore, the content of silica is preferably 0.3% by mass or more, more preferably 0.5% by mass or more, and further preferably 0.8% by mass or more. On the other hand, when the content of silica is 5.5% by mass or less, it is possible to easily prevent a decrease in adhesiveness of the pasty preparation due to excessive absorption of moisture by silica or aggregation of silica. Therefore, the content of silica is preferably 5.0% by mass or less, more preferably 3.5% by mass or less, further preferably 2.5% by mass or less, and still more preferably 2.0% by mass or less.

A ratio of mass of the silica to mass of the oil component (mass of the silica/mass of the oil component) is preferably 0.06 or more. Whereby, exudation of the pasty preparation can be easily prevented. In addition, the adhesiveness of the pasty preparation is easily improved. On the other hand, when the ratio is 5 or less, it is possible to easily prevent a decrease in the adhesiveness of the pasty preparation due to excessive absorption of moisture by silica, and the adhesiveness of the pasty preparation is easily improved. Therefore, the ratio is preferably 5 or less, more preferably 4 or less, further preferably 3 or less, and still more preferably 2 or less.

The content of water in the pasty preparation is preferably 10% by mass or more and 75% by mass or less, more preferably 20% by mass or more and 70% by mass or less, and further preferably 30% by mass or more and 65% by mass or less.

[Other Components]

In addition, a drug, a water-soluble polymer material, an adhesion enhancer, a crosslinking agent, a humectant, a pH adjuster, an antioxidant, a tackifier resin, an inorganic powder, a stabilizer, purified water, and the like can be blended in the pasty preparation. These can be used singly or in combination of two or more kinds.

[Drug]

The drug is preferably at least one selected from the group consisting of local anesthetic and pharmaceutically acceptable salt thereof (hereinafter, may be simply referred to as a local anesthetic).

When the drug is a local anesthetic, the content of the drug in the pasty preparation is preferably 0.5% by mass or more and 1.0% by mass or less. When the content of the drug is 0.5% by mass or more, drug efficacy of the drug is easily exhibited. Therefore, the content of the drug is more preferably 0.7% by mass or more, further preferably 1.0% by mass or more, still more preferably 2.0% by mass or more, and particularly preferably 2.5% by mass or more. On the other hand, when the content of the drug is 10% by mass or less, a precipitate of the drug is hardly generated, so that transdermal absorbability of the drug is easily improved. Therefore, the content of the drug is more preferably 8% by mass or less, further preferably 6% by mass or less, and still more preferably 5% by mass or less.

When the drug is a local anesthetic, a ratio of total of mass of the drug and mass of the 1-menthol to mass of the oil component [(mass of the drug+mass of the 1-menthol)/mass of the oil component] is preferably 0.10 or more and 12 or less. When the ratio is 12 or less, solubility of the drug and the 1-menthol is improved, so that generation of a precipitate in the pasty preparation can be easily prevented. Therefore, the ratio is more preferably 10 or less. On the other hand, when the ratio is 0.10 or more, it is possible to easily prevent deterioration in shape retaining properties and adhesiveness due to an excessively large oil component. Therefore, the ratio is more preferably 0.30 or more.

Examples of the local anesthetic include lidocaine, mepivacaine, dibucaine, bupivacaine, ropivacaine, levobupivacaine, tetracaine, and the like. These can be used singly or in combination of two or more kinds. The pharmaceutically acceptable salt is not particularly limited, and examples thereof include hydrochloride, phosphate, acetate, lactate, tartrate, and the like. These can be used singly or in combination of two or more kinds.

The drug is also preferably at least one selected from the group consisting of anti-inflammatory drug and pharmaceutically acceptable salt thereof (hereinafter, may be simply referred to as an anti-inflammatory drug).

When the drug is an anti-inflammatory drug, the content of the drug in the pasty preparation is preferably 0.3% by mass or more and 5% by mass or less. When the content of the drug is 0.3% by mass or more, drug efficacy of the drug is easily exhibited. Therefore, the content of the drug is more preferably 0.5% by mass or more, and further preferably 0.7% by mass or more. On the other hand, when the content of the drug is 5% by mass or less, a precipitate of the drug is hardly generated. Therefore, the content of the drug is more preferably 4% by mass or less, and further preferably 3% by mass or less.

When the drug is an anti-inflammatory drug, a ratio of total of mass of the drug and mass of the 1-menthol to mass of the oil component [(mass of the drug+mass of the 1-menthol)/mass of the oil component] is preferably 0.10 or more and 6 or less. When the ratio is 6 or less, solubility of the drug and the 1-menthol is improved, so that generation of a precipitate in the pasty preparation can be easily prevented. Therefore, the ratio is more preferably 4 or less, and further preferably 3 or less. On the other hand, when the ratio is 0.10 or more, it is possible to easily prevent deterioration in shape retaining properties and adhesiveness due to an excessively large oil component.

Examples of the anti-inflammatory drug include loxoprofen, ketoprofen, indomethacin, flurbiprofen, ibuprofen, zaltoprofen, fenbufen, pranoprofen, piroxicam, meloxicam, felbinac, diclofenac, methyl salicylate, glycol salicylate, and the like. These can be used singly or in combination of two or more kinds. Examples of the pharmaceutically acceptable salt include alkali metal salt such as sodium salt, potassium salt, and lithium salt; alkaline earth metal salt such as calcium salt and magnesium salt; and the like. These can be used singly or in combination of two or more kinds.

[Water-Soluble Polymer Material]

The pasty preparation preferably further contains a water-soluble polymer material (hereinafter, sometimes simply referred to as a water-soluble polymer). The water-soluble polymer can be dissolved in water to exhibit a thickening function. Further, by forming a crosslinked body using a crosslinking agent, adhesive force of the pasty preparation can be increased. Due to the thickening function and adhesiveness of such a water-soluble polymer, the shape retaining properties of the pasty preparation can be easily maintained.

The content of the water-soluble polymer in the pasty preparation is preferably 2% by mass or more and 20% by mass or less. When the content of the water-soluble polymer is 2% by mass or more, the effect of the water-soluble polymer is easily exhibited. Therefore, the content of the water soluble polymer is more preferably 3% by mass or more, and further preferably 5% by mass or more. On the other hand, when the content of the water-soluble polymer is 20% by mass or less, the water-soluble polymer is easily dissolved, so that the pasty preparation becomes uniform and the shape retaining properties can be easily kept constant. Therefore, the content of the water-soluble polymer is more preferably 17% by mass or less, and further preferably 15% by mass or less.

A ratio of mass of the water-soluble polymer to mass of the oil component (mass of the water-soluble polymer/mass of the oil component) is preferably 0.65 or more. This makes it easy to prevent oil floating on an adhesive surface of the oil component, and the adhesiveness of the water soluble polymer is easily exhibited. On the other hand, the upper limit of the ratio is not particularly limited, and may be, for example, 25 or less, 17 or less, 10 or less, or 5 or less.

The water-soluble polymer is preferably at least one selected from the group consisting of polyacrylic acid, salt of polyacrylic acid, cellulose derivative, polyvinyl alcohol, carboxyvinyl polymers, and gelatin, and more preferably at least one selected from the group consisting of polyacrylic acid, salt of polyacrylic acid, and cellulose derivative. These can be used singly or in combination of two or more kinds.

The polyacrylic acid and salt of polyacrylic acid are dissolved in water to exhibit thickening. Furthermore, the adhesive force of the pasty preparation can be increased by forming a crosslinked body with a crosslinking agent. Examples thereof include polyacrylic acid, sodium polyacrylate, and partially neutralized polyacrylate. These can be used singly or in combination of two or more kinds.

The cellulose derivative is dissolved in water to exhibit thickening. Furthermore, it also exhibits a function of controlling the shape retaining properties of the pasty preparation. Examples of the cellulose derivative include sodium carboxymethylcellulose, hydroxypropyl cellulose, hydroxymethyl cellulose, and the like. Among them, sodium carboxymethylcellulose is particularly preferable. These can be used singly or in combination of two or more kinds.

[Adhesion Enhancer]

Examples of the adhesion enhancer include (meth)acrylic acid-based aqueous resin emulsion such as methyl acrylate-2-ethylhexyl acrylate, acrylic acid ester-methacrylic acid ester, and methacrylic acid n-butyl acrylate copolymer. In the pasty preparation, the (meth)acrylic acid-based aqueous resin emulsion is compatible with oil components, and can easily improve adhesiveness. These can singly improve the adhesiveness of the pasty preparation, but can be used in combination of two or more kinds.

The content of the adhesion enhancer in the pasty preparation is preferably 1% by mass or more and 15% by mass or less, more preferably 3% by mass or more and 10% by mass or less, and further preferably 5% by mass or more and 8% by mass or less.

[Crosslinking Agent]

The crosslinking agent is preferably one that forms a crosslinked body such as a polyacrylic acid derivative. Whereby, the shape retaining properties of the pasty preparation can be easily maintained. Specifically, the crosslinking agent is preferably a poorly soluble polyvalent metal salt, and more preferably dihydroxyaluminum aminoacetate, magnesium aluminometasilicate, aluminum hydroxide, synthetic hydrotalcite, or the like. Among them, dihydroxyaluminum aminoacetate, magnesium aluminate metasilicate, and synthetic hydrotalcite are further preferable. These can be used singly or in combination of two or more kinds.

The content of the crosslinking agent in the pasty preparation is preferably 0.02% by mass or more and 3.5% by mass or less, and more preferably 0.03% by mass or more and 2% by mass or less. When the content is 0.02% by mass or more, a crosslinked body is easily formed, and the shape retaining properties of the pasty preparation are easily maintained. On the other hand, when the content is 3.5% by mass or less, it is possible to easily avoid deterioration in adhesiveness due to excessive formation of the crosslinked body.

[Humectant]

The humectant is preferably one that can enhance a moisturizing effect on the skin and maintain the shape retaining properties of the pasty preparation. Specifically, the humectant is preferably a water-soluble polyhydric alcohol, and more preferably glycerin, 1,3-butylene glycol, propylene glycol, dipropylene glycol, isoprene glycol, polypropylene glycol. D-sorbitol, low molecular weight polyethylene glycol, or the like. These can be used singly or in combination of two or more kinds. Among them, glycerin, propylene glycol, and D-sorbitol are further preferable. The low molecular weight polyethylene glycol means polyethylene glycol having a weight average molecular weight of less than 1000.

The content of the humectant in the pasty preparation is preferably 5% by mass or more and 60% by mass or less, more preferably 10% by mass or more and 50% by mass or less, and still more preferably 15% by mass or more and 40% by mass or less. When the content is 5% by mass or more, the shape retaining properties of the pasty preparation are easily maintained. On the other hand, when the content is 60% by mass or less, it is possible to easily avoid deterioration in the adhesiveness and shape retaining properties of the pasty preparation due to shortage of other blending components, particularly water.

[pH Adjusting Agent]

The pH adjusting agent adjusts pH of the pasty preparation. The pH adjusting agent is preferably an organic acid, and more preferably tartaric acid, lactic acid, malic acid, or the like. These can be used singly or in combination of two or more kinds.

The content of the pH adjusting agent in the pasty preparation is preferably 0.2% by mass or more and 10% by mass or less, and more preferably 0.5% by mass or more and 5% by mass or less. By blending the pH adjusting agent in a content within the range, the pH of the pasty preparation can be easily adjusted to a range of 4 to 8, and the drug in the pasty preparation can be maintained in a dissolved state to easily maintain the adhesive force and shape retaining properties of the pasty preparation.

[Antioxidant]

Examples of the antioxidant include dibutylhydroxytoluene (BHT), ascorbic acid, tocopherol, and the like. These can be used singly or in combination of two or more kinds.

[Tackifier Resin]

Examples of the tackifier resin include liquid rubbers such as polyisobutylene, rosin, glycerin ester of rosin, hydrogenated rosin, glycerin ester of hydrogenated rosin, alicyclic saturated hydrocarbon resin, aliphatic hydrocarbon resin, terpene resin, and the like. These can be used singly or in combination of two or more kinds.

[Inorganic Powder]

Examples of the inorganic powder include talc, kaolin, titanium oxide, zinc oxide, magnesium carbonate, calcium carbonate, and the like. These can be used singly or in combination of two or more kinds.

[Stabilizer]

Examples of the stabilizer include oxybenzone, sodium edetate, and the like. These can be used singly or in combination of two or more kinds.

The pasty preparation may contain other therapeutically effective drug. Furthermore, if necessary, other materials generally used for aqueous patches, for example, surfactants, solubilizing agents, preservatives, absorption promoters, flavoring agents, coloring agents, and the like may be blended.

Coating amount of the pasty preparation is preferably 3M) g/m$^2$ or more and 1400 g/m$^2$ or less. When the coating amount is 300 g/m$^2$ or more, adhesiveness and tackiness are easily sustained. Therefore, the coating amount is more preferably 400 g/m$^2$ or more, and further preferably 450 g/m$^2$ or more. On the other hand, when the coating amount is 1400 g/m$^2$ or less, cohesive force and shape retaining properties can be easily improved. Therefore, the coating amount is more preferably 1200 g/m$^2$ or less, and further preferably 1000 g/m$^2$ or less.

The adhesiveness of the pasty preparation measured by a ball tack test after storage for 3 months under refrigeration is preferably No. 10 or more as measured by a method described in Examples described later. The upper limit is not particularly limited, but may be, for example, No. 32 or less, or No. 30 or less.

The aqueous patch contains the pasty preparation, and specifically, is preferably a transdermal absorption type patch preparation containing a support, a pasty preparation, and a release layer.

The support is not particularly limited as long as it can hold the applied pasty preparation, and examples thereof include porous body such as foams, woven fabric, nonwoven fabric, films, and sheets, made of the materials such as polyethylene, polypropylene, polyvinyl chloride, polyester, nylon, polyurethane, and rayon. These can be used singly or in combination of two or more kinds as a laminated body.

The release layer is not particularly limited as long as it can cover the surface of the pasty preparation, and examples thereof include plastic films such as polyethylene, polypropylene, polyester, and polyvinyl chloride, release paper, and the like. These can be used singly or in combination of two or more kinds as a laminated body. Furthermore, such materials whose surfaces underwent silicone treatment, corona discharge treatment, embossing treatment, plasma treatment, or the like can also be used.

The aqueous patch can be produced by a known method. For example, the aqueous patch can be obtained by spreading a pasty preparation composition containing a predetermined component on a support and covering the surface of the pasty preparation with a plastic film. The obtained aqueous patch can be used by being cut into an appropriate shape and size according to affected area of disease.

This application claims benefit of priority based on Japanese Patent Application No. 2019-116551 filed on Jun. 24, 2019. The entire content of the specification of Japanese Patent Application No. 2019-116551 filed on Jun. 24, 2019 is incorporated herein by reference.

EXAMPLES

The present invention will be described below more specifically with reference to examples, but the present invention is not limited to the following examples. The present invention can be also put into practice after modifications or variations within a range meeting the gist described above and below, all of which are included in the technical scope of the present invention.

Examples 1 to 3: (Lidocaine-Containing Aqueous Patches)

Components were blended in ratios (% by mass) described in Table 1 below, and uniformly mixed to prepare pasty preparations. The obtained pasty preparations were each spread on a nonwoven fabric (support) having a basis weight of 100 g/m$^2$ so that the coating amount of the pasty preparations was 700 g/m$^2$. Subsequently, the pasty preparation surface was covered with a plastic film (release layer). Further, they were cut into a rectangle of 10 cm×14 cm to obtain aqueous patches.

Comparative Examples 1 and 2: (Lidocaine-Containing Aqueous Patches)

Components were blended in ratios (% by mass) described in Table 1 below, and aqueous patches were obtained in the same manner as in Example 1.

The obtained aqueous patches of Example 0.1 to 3 and Comparative Examples 1 and 2 were subjected to the following evaluations.

[Exudation of Pasty Preparation]

At an initial stage after preparation of each aqueous patch, the presence or absence of exudation of the pasty preparation from the support was visually observed.

[Crystal Precipitation]

Each aqueous patch was wrapped with an aluminum laminated film, and its periphery was heat-sealed, sealed, and stored in a thermostatic bath at 3° C. for 3 months (after storage for 3 months under refrigeration), then the presence or absence of precipitation of crystals of 1-menthol and lidocaine in the pasty preparation was observed using a polarizing microscope. An aqueous patch in which crystals of 1-menthol and lidocaine were not observed was evaluated as "absent", and an aqueous patch in which crystals of 1-menthol and lidocaine were observed was evaluated as "present". In particular, since the crystals of 1-menthol are characteristic needle crystals, it can be easily distinguished from the crystals of lidocaine.

[Adhesiveness]

A steel ball was rolled on the pasty preparation of each aqueous patch, and the maximum number (No.) of a ball stopped on an adhesive surface was used as a measured value, based on an inclined ball tack test method of the Japanese Pharmacopoeia. The larger the measured value, the better the adhesiveness. An initial value after the preparation of the aqueous patch and a value after the aqueous patch was wrapped with an aluminum laminated film, and its periphery was heat-sealed, sealed, and stored in a thermostatic bath at 3° C. for 3 months (after storage for 3 months under refrigeration) were each obtained.

TABLE 1

| Component of pasty preparation | | unit | Example 1 | Example 2 | Example 3 | Comparative Example 1 | Comparative Example 2 |
|---|---|---|---|---|---|---|---|
| Drug | Lidocaine | mass % | 4.0 | 4.0 | 4.0 | 4.0 | 4.0 |
| Menthol | I-menthol | mass % | 1.0 | 1.0 | 1.0 | 1.0 | 1.0 |
| Oil component | Olive oil | mass % | 0.5 | 5.0 | 15.0 | 0.0 | 20.0 |
| Silica | Light silica | mass % | 1.0 | 1.0 | 1.0 | 1.0 | 1.0 |
| Water-soluble | Sodium polyacrylate | mass % | 6.0 | 6.0 | 6.0 | 6.0 | 6.0 |

TABLE 1-continued

| Component of pasty preparation | | unit | Example 1 | Example 2 | Example 3 | Comparative Example 1 | Comparative Example 2 |
|---|---|---|---|---|---|---|---|
| polymer | Carboxymethylcellulose | mass % | 4.0 | 4.0 | 4.0 | 4.0 | 4.0 |
| | Polyacrylic acid | mass % | 2.0 | 2.0 | 2.0 | 2.0 | 2.0 |
| Adhesion enhancer | Acrylic acid-based aqueous resin emulsion | mass % | 2.0 | 2.0 | 2.0 | 2.0 | 2.0 |
| Stablizer | Sodium edetate | mass % | 0.1 | 0.1 | 0.1 | 0.1 | 0.1 |
| Crosslinking agent | Crosslinking agent | mass % | 0.2 | 0.2 | 0.2 | 0.2 | 0.2 |
| pH adjuster | pH adjuster | mass % | 2.0 | 2.0 | 2.0 | 2.0 | 2.0 |
| Inorganic powder | Titanium oxide | mass % | 0.5 | 0.5 | 0.5 | 0.5 | 0.5 |
| | Kaolin | mass % | 1.5 | 1.5 | 1.5 | 1.5 | 1.5 |
| Humectant | Propylene glycol | mass % | 3.0 | 3.0 | 3.0 | 3.0 | 3.0 |
| | Concentrated glycerin | mass % | 14.0 | 14.0 | 14.0 | 14.0 | 14.0 |
| | D-sorbitol | mass % | 7.0 | 7.0 | 7.0 | 7.0 | 7.0 |
| Water | Purified water | mass % | 51.3 | 46.8 | 36.8 | 51.8 | 31.8 |
| Light silica/Oil component (mass ratio) | | | 2.00 | 0.20 | 0.07 | — | 0.05 |
| (Drug + I-menthol)/Oil component (mass ratio) | | | 10.00 | 1.00 | 0.33 | — | 0.25 |
| Water-soluble polymer/Oil component (mass ratio) | | | 24.00 | 2.40 | 0.80 | — | 0.60 |
| Oil component/I-menthol (mass ratio) | | | 0.50 | 5.00 | 15.00 | 0.00 | 20.00 |
| Exudation of pasty preparation from support | | | absent | absent | absent | absent | present |
| Crystal precipitation of Drug(Lidocaine) and I-menthol (after storage for 3 months under refrigeration) | | | absent | absent | absent | present | absent |
| Adhesiveness (initial value) | | | No. 24 | No. 22 | No. 14 | No. 20 | No. 3 |
| Adhesiveness (after storage for 3 months under refrigeration) | | | No. 23 | No. 23 | No. 15 | No. 12 | No. 4 |

As shown in Table 1, in Examples 1 to 3, the drug was not precipitated in the pasty preparations, and the shape retaining properties and adhesiveness of the pasty preparations were also good. Further, there was also no exudation of the pasty preparation. On the other hand, in Comparative Example 1, there was precipitation of crystals of the drug and 1-menthol in the pasty preparation. In Comparative Example 2, the pasty preparation exuded from the support, the shape retaining properties were deteriorated, and the adhesiveness was remarkably poor.

Examples 4 to 6: (Ketoprofen-Containing Aqueous Patches)

Components were blended in ratios (% by mass) described in Table 2 below, and uniformly mixed to prepare pasty preparations. The obtained pasty preparations were each spread on a nonwoven fabric (support) having a basis weight of 90 g/m² so that the coating amount of the pasty preparations was 50) g/m². Subsequently, the pasty preparation surface was covered with a plastic film (release layer). Further, they were cut into a rectangle of 7 cm×10 cm to obtain aqueous patches.

Comparative Examples 3 and 4: (Ketoprofen-Containing Aqueous Patches)

Components were blended in ratios described in Table 2 below, and aqueous patches were prepared in the same manner as in Examples 4 to 6.

For the obtained aqueous patches of Examples 4 to 6 and Comparative Examples 3 and 4, exudation of the pasty preparation, crystal precipitation, and adhesiveness were evaluated in the same manner as in Example 1.

TABLE 2

| Component of pasty preparation | | unit | Example 4 | Example 5 | Example 6 | Comparative Example 3 | Comparative Example 4 |
|---|---|---|---|---|---|---|---|
| Drug | Ketoprofen | mass % | 1.0 | 1.0 | 1.0 | 1.0 | 1.0 |
| Menthol | I-menthol | mass % | 1.0 | 1.0 | 1.0 | 1.0 | 1.0 |
| Oil component | Corn oil | mass % | 1.0 | 1.0 | 15.0 | 0.0 | 15.0 |
| Silica | Light silica | mass % | 0.2 | 5.0 | 5.0 | 0.0 | 6.0 |
| Water-soluble polymer | Partially neutralized polyacrylic acid | mass % | 6.0 | 6.0 | 6.0 | 6.0 | 6.0 |
| | Carboxymethylcellulose | mass % | 3.5 | 3.5 | 3.5 | 3.5 | 3.5 |
| | Polyacrylic acid | mass % | 1.0 | 1.0 | 1.0 | 1.0 | 1.0 |
| Adhesion enhancer | Acrylic acid-based aqueous resin emulsion | mass % | 6.0 | 6.0 | 6.0 | 6.0 | 6.0 |
| Stablizer | Sodium edetate | mass % | 0.1 | 0.1 | 0.1 | 0.1 | 0.1 |
| Crosslinking agent | Crosslinking agent | mass % | 0.1 | 0.1 | 0.1 | 0.1 | 0.1 |
| pH adjuster | pH adjuster | mass % | 1.0 | 1.0 | 1.0 | 1.0 | 1.0 |
| Humectant | Propylene glycol | mass % | 10.0 | 10.0 | 10.0 | 10.0 | 10.0 |
| | Concentrated glycerin | mass % | 12.0 | 12.0 | 12.0 | 12.0 | 12.0 |
| | D-sorbitol | mass % | 10.5 | 10.5 | 10.5 | 10.5 | 10.5 |
| Water | Purified water | mass % | 46.6 | 41.8 | 27.8 | 47.8 | 26.8 |
| Light silica/Oil component (mass ratio) | | | 0.20 | 5.00 | 0.33 | — | 0.40 |
| (Drug + I-menthol)/Oil component (mass ratio) | | | 2.00 | 2.00 | 0.13 | — | 0.13 |

TABLE 2-continued

| Component of pasty preparation | unit | Example 4 | Example 5 | Example 6 | Comparative Example 3 | Comparative Example 4 |
|---|---|---|---|---|---|---|
| Water-soluble polymer/Oil component (mass ratio) | | 10.50 | 10.50 | 0.70 | — | 0.70 |
| Oil component/I-menthol (mass ratio) | | 1.00 | 1.00 | 15.00 | 0.00 | 15.00 |
| Exudation of pasty preparation from support | | absent | absent | absent | absent | absent |
| Crystal precipitation of Drug(Ketoprofen) and I-menthol (after storage for 3 months under refrigeration) | | absent | absent | absent | present | absent |
| Adhesiveness (initial value) | | No. 18 | No. 16 | No. 12 | No. 19 | No. 5 |
| Adhesiveness (after storage for 3 months under refrigeration) | | No. 18 | No. 16 | No. 12 | No. 9 | No. 6 |

As shown in Table 2, in Examples 4 to 6, there was no precipitation of crystals of the drug and 1-menthol in the pasty preparations, and the adhesiveness (Nos. 12 to 18) and shape retaining properties were also good. On the other hand, in Comparative Example 3, there was precipitation of crystals of the drug and 1-menthol in the pasty preparation, and the adhesiveness of the pasty preparation was also low. In Comparative Example 4, there was no crystal precipitation in the pasty preparation, but secondary aggregation occurred because the amount of silica was too large, and unevenness of the pasty preparation was caused in the preparation. The adhesiveness was also remarkably low as No. 6.

Examples 7 to 10: (Lidocaine-Containing Aqueous Patches)

Components were blended in ratios (% by mass) described in Table 3 below, and uniformly mixed to prepare pasty preparations. The obtained pasty preparations were each spread on a nonwoven fabric (support) having a basis weight of 110 g/m$^2$ so that the coating amount of the pasty preparations was 1000 g/m$^2$. Subsequently, the pasty preparation surface was covered with a plastic film (release layer). Further, they were cut into a rectangle of 10 cm×14 cm to obtain aqueous patches.

Comparative Example 5: (Lidocaine-Containing Aqueous Patch)

Components were blended in ratios (% by mass) described in Table 3 below, and an aqueous patch was obtained in the same manner as in Examples 7 to 10.

For the obtained aqueous patches of Examples 7 to 10 and Comparative Example 5, exudation of the pasty preparation, crystal precipitation, and adhesiveness were evaluated in the same manner as in Example 1.

TABLE 3

| Component of pasty preparation | | unit | Example 7 | Example 8 | Example 9 | Example 10 | Comparative Example 5 |
|---|---|---|---|---|---|---|---|
| Drug | Lidocaine | mass % | 4.0 | 4.0 | 4.0 | 4.0 | 4.0 |
| Menthol | I-menthol | mass % | 3.0 | 3.0 | 3.0 | 3.0 | 3.0 |
| Oil component | Oleic acid | mass % | 4.0 | 0.0 | 2.0 | 0.0 | 0.0 |
| | Liquid paraffin | mass % | 0.0 | 4.0 | 0.0 | 0.0 | 0.0 |
| | Isopropyl myristate | mass % | 0.0 | 0.0 | 2.0 | 0.0 | 0.0 |
| | Tocopherol acetate | mass % | 0.0 | 0.0 | 0.0 | 2.0 | 0.0 |
| | Crotamiton | mass % | 0.0 | 0.0 | 0.0 | 2.0 | 0.0 |
| Silica | Light silica | mass % | 2.5 | 2.5 | 2.5 | 2.5 | 2.5 |
| Water-soluble polymer | Partially neutralized polyacrylic acid | mass % | 6.0 | 6.0 | 6.0 | 6.0 | 6.0 |
| | Carboxymethylcellulose | mass % | 4.0 | 4.0 | 4.0 | 4.0 | 4.0 |
| | Polyacrylic acid | mass % | 2.0 | 2.0 | 2.0 | 2.0 | 2.0 |
| Adhesion enhancer | Acrylic acid-based aqueous resin emulsion | mass % | 6.0 | 6.0 | 6.0 | 6.0 | 6.0 |
| Stabilizer | Sodium edetate | mass % | 0.1 | 0.1 | 0.1 | 0.1 | 0.1 |
| Crosslinking agent | Crosslinking agent | mass % | 0.1 | 0.1 | 0.1 | 0.1 | 0.1 |
| pH adjuster | pH adjuster | mass % | 0.5 | 0.5 | 0.5 | 0.5 | 0.5 |
| Inorganic powder | Titanium oxide | mass % | 0.5 | 0.5 | 0.5 | 0.5 | 0.5 |
| Humectant | Propylene glycol | mass % | 6.0 | 6.0 | 6.0 | 6.0 | 6.0 |
| | Concentrated glycerin | mass % | 20.0 | 20.0 | 20.0 | 20.0 | 20.0 |
| | D-sorbitol | mass % | 7.0 | 7.0 | 7.0 | 7.0 | 7.0 |
| Water | Purified water | mass % | 34.3 | 34.3 | 34.3 | 34.3 | 38.3 |
| Light silica/Oil component (mass ratio) | | | 0.63 | 0.63 | 0.63 | 0.63 | — |
| (Drug +] I-menthol)/Oil component (mass ratio) | | | 1.75 | 1.75 | 1.75 | 1.75 | — |
| Water-soluble polymer/Oil component (mass ratio) | | | 3.00 | 3.00 | 3.00 | 3.00 | — |
| Oil component/I-menthol (mass ratio) | | | 1.33 | 1.33 | 1.33 | 1.33 | 0.00 |
| Exudation of pasty preparation from support | | | absent | absent | absent | absent | absent |
| Crystal precipitation of Drug (Lidocaine) and I-menthol (after storage for 3 months under refrigeration) | | | absent | absent | absent | absent | present |
| Adhesiveness (initial value) | | | No.25 | No.25 | No.17 | No.26 | No.20 |
| Adhesiveness (after storage for 3 months under refrigeration) | | | No.24 | No.24 | No.17 | No.26 | No.12 |

As shown in Table 3, Examples 7 to 10 contained oil components of oleic acid, liquid paraffin, isopropyl myristate, tocopherol acetate, and crotamiton alone or in combination of two or more kinds, and there was no precipitation of crystals of the drug and 1-menthol after storage for 3 months under refrigeration, and the shape retaining properties and adhesiveness of the pasty preparations were also good. On the other hand, in Comparative Example 5 not containing these oil components, precipitation of crystals of the drug and 1-menthol was observed in the pasty preparation.

Examples 11 to 13: (High Concentration 1-Menthol/Lidocaine-Containing Aqueous Patches)

Components were blended in ratios (% by mass) described in Table 4 below, and aqueous patches were obtained in the same manner as in Example 1.

Comparative Examples 6 to 8: (Lidocaine-Containing Aqueous Patches)

Components were blended in ratios (% by mass) described in Table 4 below, and aqueous patches were obtained in the same manner as in Example 1.

For the obtained aqueous patches of Examples 11 to 13 and Comparative Examples 6 to 8, exudation of the pasty preparation and initial adhesiveness were evaluated in the same manner as in Example 1. Further, initial crystal precipitation after preparation of the aqueous patch was also evaluated. Furthermore, an in vitro skin permeation test of a drug using the following excised abdominal skin of a hairless rat was performed to evaluate drug permeability.

[Drug Permeability]

An abdominal skin of a hairless rat was excised, and put on a Franz diffusion cell. A phosphate buffer solution was then injected, and the buffer solution was stirred while keeping the temperature at 37° C. Subsequently, an aqueous patch cut into a circle with a diameter of 14 mm was applied to the excised skin, and the amount of drug transferred from the aqueous patch to the buffer solution through the skin (permeation amount) was measured using a liquid chromatography equipment. Specifically, cumulative permeation amount ($\mu g/cm^2$) of lidocaine after 24 hours from start of the test was measured.

TABLE 4

| Component of pasty preparation | | unit | Example 11 | Example 12 | Example 13 | Comparative Example 6 | Comparative Example 7 | Comparative Example 8 |
|---|---|---|---|---|---|---|---|---|
| Drug | Lidocaine | mass % | 4.0 | 4.0 | 4.0 | 4.0 | 4.0 | 4.0 |
| Menthol | I-menthol | mass % | 1.0 | 4.0 | 8.0 | 0.0 | 0.0 | 4.0 |
| Oil component | Castor oil | mass % | 8.0 | 8.0 | 8.0 | 0.0 | 8.0 | 0.0 |
| Silica | Light silica | mass % | 0.5 | 0.5 | 0.5 | 0.5 | 0.5 | 0.5 |
| Water-soluble polymer | Partially neutralized polyacrylic acid | mass % | 5.0 | 5.0 | 5.0 | 5.0 | 5.0 | 5.0 |
| | Carboxymethylcellulose | mass % | 4.0 | 4.0 | 4.0 | 4.0 | 4.0 | 4.0 |
| | Polyacrylic acid | mass % | 2.0 | 2.0 | 2.0 | 2.0 | 2.0 | 2.0 |
| Adhesion enhancer | Acrylic acid-based aqueous resin emulsion | mass % | 8.0 | 8.0 | 8.0 | 8.0 | 8.0 | 8.0 |
| Stabilizer | Sodium edetate | mass % | 0.1 | 0.1 | 0.1 | 0.1 | 0.1 | 0.1 |
| Crosslinking agent | Crosslinking agent | mass % | 1.1 | 1.1 | 1.1 | 1.1 | 1.1 | 1.1 |
| pH adjuster | pH adjuster | mass % | 1.0 | 1.0 | 1.0 | 1.0 | 1.0 | 1.0 |
| Inorganic powder | Titanium oxide | mass % | 0.5 | 0.5 | 0.5 | 0.5 | 0.5 | 0.5 |
| | Kaolin | mass % | 1.5 | 1.5 | 1.5 | 1.5 | 1.5 | 1.5 |
| Humectant | Propylene glycol | mass % | 3.0 | 3.0 | 3.0 | 3.0 | 3.0 | 3.0 |
| | Concentrated glycerin | mass % | 18.0 | 18.0 | 18.0 | 18.0 | 18.0 | 18.0 |
| | D-sorbitol | mass % | 7.0 | 7.0 | 7.0 | 7.0 | 7.0 | 7.0 |
| Water | Purified water | mass % | 35.3 | 32.3 | 28.3 | 44.3 | 36.3 | 40.3 |
| Light silica/Oil component (mass ratio) | | | 0.06 | 0.06 | 0.06 | — | 0.06 | — |
| (Drug + I-menthol)/Oil component (mass ratio) | | | 0.63 | 1.00 | 1.50 | — | 0.50 | — |
| Water-soluble polymer/Oil component (mass ratio) | | | 1.38 | 1.38 | 1.38 | — | 1.38 | — |
| Oil component/I-menthol (mass ratio) | | | 8.00 | 2.00 | 1.00 | — | — | 0.00 |
| Exudation of pasty preparation from support | | | absent | absent | absent | absent | absent | absent |
| Crystal precipitation of I-menthol (initial) | | | absent | absent | absent | — | — | present |
| Crystal precipitation of Drug(Lidocaine) (initial) | | | absent | absent | absent | present | absent | present |
| Adhesiveness (initial value) | | | No. 26 | No. 26 | No. 24 | No. 20 | No. 22 | No. 18 |
| Cumulative permeation amount ($\mu g/cm^2$) of Lidocaine after 24 hours from start of test | | | 77.6 | 86.8 | 124 | 26.1 | 49.4 | 68.9 |

As shown in Table 4, the aqueous, patch of Comparative Example 6 did not contain 1-menthol and an oil component, and crystals of the drug were precipitated, so that the permeation amount was significantly low. Comparative Example 7 did not contain 1-menthol, and the permeation amount of the drug was low. The aqueous patch of Comparative Example 8 contained 1-menthol at the same content as that of the aqueous patch of Example 12 but did not contain an oil component, crystals of both the drug and For the obtained aqueous patches of Examples 14 to 18 and Comparative Examples 9 to 11, exudation of the pasty preparation was evaluated in the same manner as in Example 1. Further, crystal precipitation was evaluated in the same manner as in Example 1 except that the storage condition was set to 1 month, and adhesiveness was evaluated in the same manner as in Example 1 except that the storage condition was set to 40° C. for 1, month.

TABLE 5

| Component of pasty preparation | | unit | Example 14 | Example 15 | Example 16 | Example 17 | Example 18 | Comparative Example 9 | Comparative Example 10 | Comparative Example 11 |
|---|---|---|---|---|---|---|---|---|---|---|
| Drug | Lidocaine | mass % | 4.0 | 4.0 | — | — | — | 4.0 | 4.0 | 4.0 |
| | Ketoprofen | mass % | — | — | 2.0 | 2.0 | 2.0 | — | — | — |
| Menthol | Menthol | mass % | 5.0 | 10.0 | 0.5 | 5.0 | 10.0 | 1.0 | 11.0 | 1.0 |
| Oil component | Olive oil | mass % | 19.0 | 19.0 | — | — | — | 5.0 | 5.0 | 5.0 |
| | Corn oil | mass % | — | — | 0.2 | 19.0 | 19.0 | — | — | — |
| Silica | Silica | mass % | 0.1 | 5.5 | 0.1 | 0.1 | 5.5 | 0.0 | 1.0 | 6.0 |
| Water-soluble polymer | Sodium polyacrylate | mass % | 6.0 | 6.0 | 6.0 | 6.0 | 6.0 | 6.0 | 6.0 | 6.0 |
| | Carboxymethylcellulose | mass % | 4.4 | 4.0 | 3.5 | 5.4 | 3.5 | 4.0 | 4.0 | 4.0 |
| | Polyacrylic acid | mass % | 2.0 | 2.0 | 1.0 | 1.0 | 1.0 | 2.0 | 2.0 | 2.0 |
| Adhesion enhancer | Acrylic acid-based aqueou sresin emulsion | mass % | 2.0 | 2.0 | 6.0 | 6.0 | 6.0 | 2.0 | 2.0 | 2.0 |
| Stabilizer | Sodium edetate | mass % | 0.1 | 0.1 | 0.1 | 0.1 | 0.1 | 0.1 | 0.1 | 0.1 |
| Crosslinking agent | Crosslinking agent | mass % | 0.2 | 0.2 | 0.1 | 0.1 | 0.1 | 0.2 | 0.2 | 0.2 |
| pH adjuster | pH adjuster | mass % | 2.0 | 2.0 | 1.0 | 1.0 | 1.0 | 2.0 | 2.0 | 2.0 |
| Inorganic powder | Titanium oxide | mass % | 0.5 | 0.5 | — | — | — | 0.5 | 0.5 | 0.5 |
| | Kaolin | mass % | 1.5 | 1.5 | — | — | — | 1.5 | 1.5 | 1.5 |
| Humectant | Propylene glycol | mass % | 3.0 | 3.0 | 10.0 | 10.0 | 10.0 | 3.0 | 3.0 | 3.0 |
| | Concentrated glycerin | mass % | 14.0 | 14.0 | 12.0 | 12.0 | 12.0 | 14.0 | 14.0 | 14.0 |
| | D-sorbitol | mass % | 7.0 | 7.0 | 10.5 | 10.5 | 10.5 | 7.0 | 7.0 | 7.0 |
| Water | Purified water | mass % | 29.2 | 19.2 | 47.0 | 21.8 | 13.3 | 47.7 | 36.7 | 41.7 |
| Light silica/Oil component (mass ratio) | | | 0.01 | 0.29 | 0.50 | 0.01 | 0.29 | 0.00 | 0.20 | 1.20 |
| (Drug + l-menthol) /Oil component (mass ratio) | | | 0.47 | 0.74 | 12.50 | 0.37 | 0.63 | 1.00 | 3.00 | 1.00 |
| Water-soluble polymer/ Oil component (mass ratio) | | | 0.65 | 0.63 | 52.50 | 0.65 | 0.55 | 2.40 | 2.40 | 2.40 |
| Oil component/l-menthol (mass ratio) | | | 3.80 | 1.90 | 0.40 | 3.80 | 1.90 | 5.00 | 0.45 | 5.00 |
| Exudation of pasty preparation from support | | | absent | absent | absent | absent | absent | absent | absent | absent |
| Crystal precipitation of Drug and l-menthol (after storage for 1 month under refrigeration) | | | absent | absent | absent | absent | absent | absent | absent | absent |
| Adhesiveness (initial) (No.) | | | 12 | 15 | 20 | 18 | 15 | 22 | 0 | 0 |
| Adhesiveness (40° C. for 1 month) | | | 10 | 4 | 16 | 10 | 4 | 18 | 0 | 0 |

1-menthol were precipitated, and the permeation amount of the drug was lower than that of Example 12.

On the other hand, in the aqueous patches of Examples 11 to 13, the content of the oil component was the same and the content of 1-menthol was changed, but the permeation amount of lidocaine increased in correlation with the 1-menthol content. Among them, the aqueous patch of Example 13 showed the highest permeation amount of lidocaine. From this result, it can be seen that the aqueous patch of the embodiment of the present invention can stably maintain the dissolved state of 1-menthol for a long period of time, and also has high transdermal absorbability of the drug.

Examples 14 and 15 and Comparative Examples 9 to 11: (Lidocaine-Containing Aqueous Patches)

Aqueous patches were obtained in the same manner as in Example 2 except that components were blended in ratios (% by mass) described in Table 5 below.

Examples 16 to 18: (Ketoprofen-Containing Aqueous Patches)

Aqueous patches were obtained in the same manner as in Example 4 except that components were blended in ratios (% by mass) described in Table 5 below.

As shown in Table 5, the aqueous patch of Comparative Example 9 did not contain silica, and there was no initial exudation of the pasty preparation, but after storage at 40° C. for 1 month, there was exudation at an end of the support. The aqueous patch of Comparative Example 10 had a large amount of 1-menthol, the oil component floated on the surface of the pasty preparation, and no adhesive force was exhibited. The aqueous patch of Comparative Example 11 had a large amount of silica, the shape retaining properties were poor, and the adhesive force was not exhibited at all.

On the other hand, in Examples 1.4 to 18, the drug was not precipitated in the pasty preparations, the shape retaining properties of the pasty preparations were also good, and there was also no exudation of the pasty preparation. Further, it was possible to reduce decrease in adhesiveness under a high temperature condition of 40° C. In the aqueous patch of Example 17, there is a possibility that crystals slightly precipitate after storage for 3 months under refrigeration.

The invention claimed is:
1. An aqueous patch comprising, in a pasty preparation, 1-menthol: 0.5% by mass or more and 10% by mass or less,
an oil component: 0.2% by mass or more and 19% by mass or less;

silica: 0.1% by mass or more and 5.5% by mass or less;
a drug;
a water-soluble polymer material; and
water,
wherein the drug comprises at least one selected from the group consisting of lidocaine and a pharmaceutically acceptable salt thereof,
wherein the oil component comprises castor oil,
wherein the ratio of total mass of the drug and the 1-menthol to mass of the oil component is 0.3 or more and 12 or less,
wherein the pasty preparation does not comprise loxoprofen or a pharmaceutically acceptable salt thereof, wherein the pasty preparation does not comprise methyl salicylate, and
wherein the pasty preparation does not comprise polybutene.

2. The aqueous patch according to claim 1, comprising, in the pasty preparation,
the drug: 0.5% by mass or more and 10% by mass or less.

3. The aqueous patch according to claim 2, wherein the ratio of total mass of the drug and the 1-menthol to mass of the oil component is 0.63 or more and 12 or less.

4. The aqueous patch according to claim 1, wherein the ratio of mass of the silica to mass of the oil component is 0.06 or more.

5. The aqueous patch according to claim 1, wherein the ratio of mass of the water-soluble polymer material to mass of the oil component is 0.65 or more.

6. The aqueous patch according to claim 1, wherein the silica is a powder having a specific surface area of 30 m$^2$/g or more and 420 m$^2$/g or less as measured by a specific surface area measurement method specified in JIS Z 8830.

* * * * *